US009579453B1

(12) United States Patent
Brasington

(10) Patent No.: US 9,579,453 B1
(45) Date of Patent: Feb. 28, 2017

(54) TWO-STEP AUTO-INJECTION DEVICE

(71) Applicant: Chalbourne Brasington, Greenville, SC (US)

(72) Inventor: Chalbourne Brasington, Greenville, SC (US)

(73) Assignee: Chalbourne Brasington, Greenville, SC (US)

( * ) Notice: Subject to any disclaimer, the term of this patent is extended or adjusted under 35 U.S.C. 154(b) by 0 days.

(21) Appl. No.: 15/046,782

(22) Filed: Feb. 18, 2016

(51) Int. Cl.
| A61M 5/168 | (2006.01) |
| A61M 5/158 | (2006.01) |
| A61M 5/162 | (2006.01) |
| A61M 5/145 | (2006.01) |
| A61M 5/20 | (2006.01) |
| A61M 5/31 | (2006.01) |

(52) U.S. Cl.
CPC ............ *A61M 5/168* (2013.01); *A61M 5/145* (2013.01); *A61M 5/158* (2013.01); *A61M 5/162* (2013.01); *A61M 5/2033* (2013.01); *A61M 2005/1585* (2013.01); *A61M 2005/208* (2013.01); *A61M 2005/2013* (2013.01); *A61M 2005/2026* (2013.01); *A61M 2005/2073* (2013.01); *A61M 2005/3132* (2013.01)

(58) Field of Classification Search
CPC .... A61M 2005/208; A61M 2005/2013; A61M 2005/2026; A61M 2005/2073; A61M 2005/3132; A61M 5/2033
See application file for complete search history.

(56) References Cited

U.S. PATENT DOCUMENTS

| 3,605,744 | A | * | 9/1971 | Dwyer | ................ A61M 5/2033 604/139 |
| 4,529,403 | A | | 7/1985 | Kamstra | |
| 4,822,340 | A | | 4/1989 | Kamstra | |
| 5,092,842 | A | * | 3/1992 | Bechtold | ................ A61M 5/20 604/135 |
| 5,383,864 | A | | 1/1995 | van den Heuvel | |
| 5,709,668 | A | | 1/1998 | Wacks | |
| 7,442,185 | B2 | | 10/2008 | Amark et al. | |
| 2005/0277886 | A1 | | 12/2005 | Hommann et al. | |
| 2007/0017532 | A1 | * | 1/2007 | Wyrick | ............... A61M 5/2033 128/898 |
| 2011/0106008 | A1 | | 5/2011 | Kronestedt | |

(Continued)

*Primary Examiner* — Laura Bouchelle
*Assistant Examiner* — Anh Bui
(74) *Attorney, Agent, or Firm* — Dority & Manning, P.A.

(57) ABSTRACT

An auto-injection device for delivery of a fluid medicament is provided. The device includes an ampoule having a fluid medicament contained between first and second stoppers; a first sleeve movable along the longitudinal direction relative to the ampoule; a second sleeve at least partially surrounding the ampoule and movable along the longitudinal direction relative to the ampoule; and a needle. The first sleeve is movable along the longitudinal direction relative to the second sleeve and the ampoule between a first position and a second position. The needle is unexposed in the first position but exposed along the longitudinal direction in the second position. The second sleeve is also movable along the longitudinal direction relative to the ampoule between a first position and a second position. The needle is fluidly isolated from the medicament in the first position and is in fluid communication with the medicament in the second position.

19 Claims, 4 Drawing Sheets

(56) References Cited

U.S. PATENT DOCUMENTS

2014/0081239 A1\* 3/2014 Cronenberg ............ A61M 5/50
604/506
2015/0051578 A1\* 2/2015 Herr ........................ A61M 5/24
604/506

\* cited by examiner

TWO-STEP AUTO-INJECTION DEVICE

FIELD OF THE INVENTION

The present disclosure relates generally to auto-injection devices, and more particularly to a two-step auto-injection device and method for delivering a fluid medicament.

BACKGROUND OF THE INVENTION

Auto-injection devices are utilized in a variety of settings, typically to treat medical emergencies. For example, anaphylaxis is a serious medical emergency that can be fatal if not treated quickly. The most common causes of anaphylaxis include food allergies (e.g., nut or shellfish allergies) and insect bites or stings. Certain medications can also cause anaphylaxis. Symptoms of anaphylaxis include an itchy rash, throat swelling, and low blood pressure. Rapid diagnosis and immediate injection of intramuscular epinephrine is often critical to prevent a fatal outcome, as muscles have larger and more blood vessels than subcutaneous tissue and intramuscular injections usually have faster rates of absorption than subcutaneous or intradermal injections. Death from anaphylaxis occurs most often in teenagers and young adults and is directly related to receiving injected epinephrine too late, inaccurately (e.g., outside the muscle), or not at all. Anaphylaxis most often occurs unexpectedly and in the absence of a trained health care professional. Because exposure is unpredictable, the reaction may occur rapidly, and the patient may not be near medical help at the time of exposure, patients who are subject to severe anaphylaxis must carry epinephrine at all times. It is also necessary that the patient be able to self-administer the epinephrine during an anaphylactic attack in an efficient, simple manner.

Currently available auto-injection devices are generally cylindrical in shape and include a spring-activated concealed needle that, when triggered, springs forward to simultaneously pierce the skin and deliver a dose of epinephrine or other medicament. Such devices are designed for single dose intramuscular injection for emergency treatment of anaphylaxis.

Recent studies indicate a number of problems with the aforementioned automatic injection devices. These devices are bulky, difficult to use, and are considered burdensome to the user. Many patients are noncompliant when prescribed these devices and do not carry one with them at all times for various reasons including problems with size, shape and appearance. Further, these devices have a counter-intuitive design that can promote accidental misfiring of a device into the palm of the user's hand rather than into the thigh or other suitable area. In addition, because the dose of epinephrine is delivered at the same time that the needle is injected below the skin in a single step, there is a possibility of injection and dispersion of the epinephrine before the needle reaches the musculature.

Therefore, it can be appreciated that anaphylaxis remains an important and avoidable cause of death and that currently available automatic injection devices have a number of problems associated with their design and function. These problems can contribute to incorrect use, misuse, and not carrying the unit as prescribed (non-compliance), resulting in adverse outcomes.

As such, a need currently exists for an improved auto-injection device for rapid injection of a fluid medicament to the desired location.

SUMMARY OF THE INVENTION

Aspects and advantages of the invention will be set forth in part in the following description, or may be obvious from the description, or may be learned through practice of the invention.

In accordance with one embodiment of the present disclosure, an auto-injection device defining a longitudinal direction is contemplated. The auto-injection device includes an ampoule, a first sleeve, a second sleeve, and a needle. The ampoule includes a fluid medicament contained between a first stopper located towards a proximal end of the ampoule and a second stopper located towards a distal end of the ampoule. The first sleeve is movable along the longitudinal direction relative to the ampoule, while the second sleeve at least partially surrounds the ampoule and is movable along the longitudinal direction relative to the ampoule. Further, the first sleeve is movable along the longitudinal direction relative to the second sleeve and the ampoule between a first position and a second position, wherein in the first position the needle is unexposed along the longitudinal direction and in the second position the needle is exposed along the longitudinal direction. In addition, the second sleeve is movable along the longitudinal direction relative to the ampoule between a first position and a second position, wherein in the first position the needle is fluidly isolated from the fluid medicament and in the second position the needle is in fluid communication with the fluid medicament.

In one particular embodiment of the present disclosure, the auto-injection device can be a two-step fluid medicament delivery device. For instance, in a first step, the needle can pierce a surface of skin when the first sleeve is in the second position. Further, in a second step, fluid medicament can be delivered intramuscularly when the second sleeve is in the second position.

In another embodiment of the present disclosure, an opening can be located along a proximal end of the first sleeve, wherein the proximal end of the needle is movable through the opening when the first sleeve is moved to the second position.

In still another embodiment of the present disclosure, the needle can be fixed to the second sleeve.

In yet another embodiment of the present disclosure, a biasing element can be contained within the ampoule towards the distal end of the ampoule, wherein the biasing element (e.g., a spring or a compressed gas) exerts a biasing force on the second stopper towards the first stopper.

In an additional embodiment of the present disclosure, the auto-injection device can further include a removable safety, wherein the removable safety prevents movement of the first sleeve from the first position to the second position, prevents movement of the second sleeve from the first position to the second position, or both when not removed.

In another embodiment of the present disclosure, the ampoule can include glass.

In still another embodiment of the present disclosure, a plastic housing can surround the ampoule.

In one more embodiment of the present disclosure, the first sleeve and the second sleeve can each include a plastic.

In yet another embodiment of the present disclosure, the fluid medicament can contain epinephrine.

In an additional embodiment of the present disclosure, the auto-injection device can have a maximum length in the longitudinal direction of less than 150 millimeters.

In accordance with another embodiment of the present disclosure, a method for delivering a dose of fluid medicament via an auto-injection device is contemplated. The device defines a longitudinal direction and includes an ampoule containing a fluid medicament contained between a first stopper located towards a proximal end of the ampoule and a second stopper located towards a distal end of the ampoule; a first sleeve movable in the longitudinal direction relative to the ampoule; a second sleeve at least partially surrounding the ampoule and movable along the longitudinal direction relative to the ampoule; and a needle. The method includes positioning the proximal end of the auto-injection device against a surface of the skin, wherein the longitudinal direction of the auto-injection device is generally perpendicular to the surface of skin; piercing the surface of skin and underlying tissue with the needle by pressing the proximal end of the auto-injection device against the surface of skin until the first sleeve moves from a first position to a second position in a first step; and delivering the fluid medicament intramuscularly by pressing the proximal end of the auto-injection device against the surface of skin until the second sleeve moves from a first position to a second position in a second step.

In one particular embodiment of the present disclosure, the proximal end of the first sleeve can contact a proximal end of the second sleeve when the first sleeve is in the second position.

In another particular embodiment of the present disclosure, the proximal end of the second sleeve can contact the proximal end of a housing surrounding the ampoule when the second sleeve is in the second position.

In yet another embodiment of the present disclosure, a proximal end of the first sleeve can include an opening covered with a material to maintain sterility of the auto-injection device prior to use, wherein the material is removed prior to positioning the proximal end of the auto-injection device against the surface of skin, or wherein the material is pierced by the needle by pressing the proximal end of the auto-injection device against the surface of skin until the first sleeve moves from the first position to the second position in the first step.

In still another embodiment of the present disclosure, a removable safety can prevent the first sleeve from sliding against the second sleeve, can prevent the second sleeve from sliding against the ampoule, or both when the safety is installed (i.e., not removed), wherein the removable safety is removed prior to positioning the proximal end of the auto-injection device against the surface of skin.

In an additional embodiment of the present disclosure, a biasing element can be contained within the ampoule towards the distal end of the ampoule, wherein the biasing element exerts a biasing force on the second stopper towards the first stopper to facilitate delivery of the fluid medicament when the second sleeve is in the second position.

In one more embodiment of the present disclosure, the fluid medicament can contain epinephrine.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
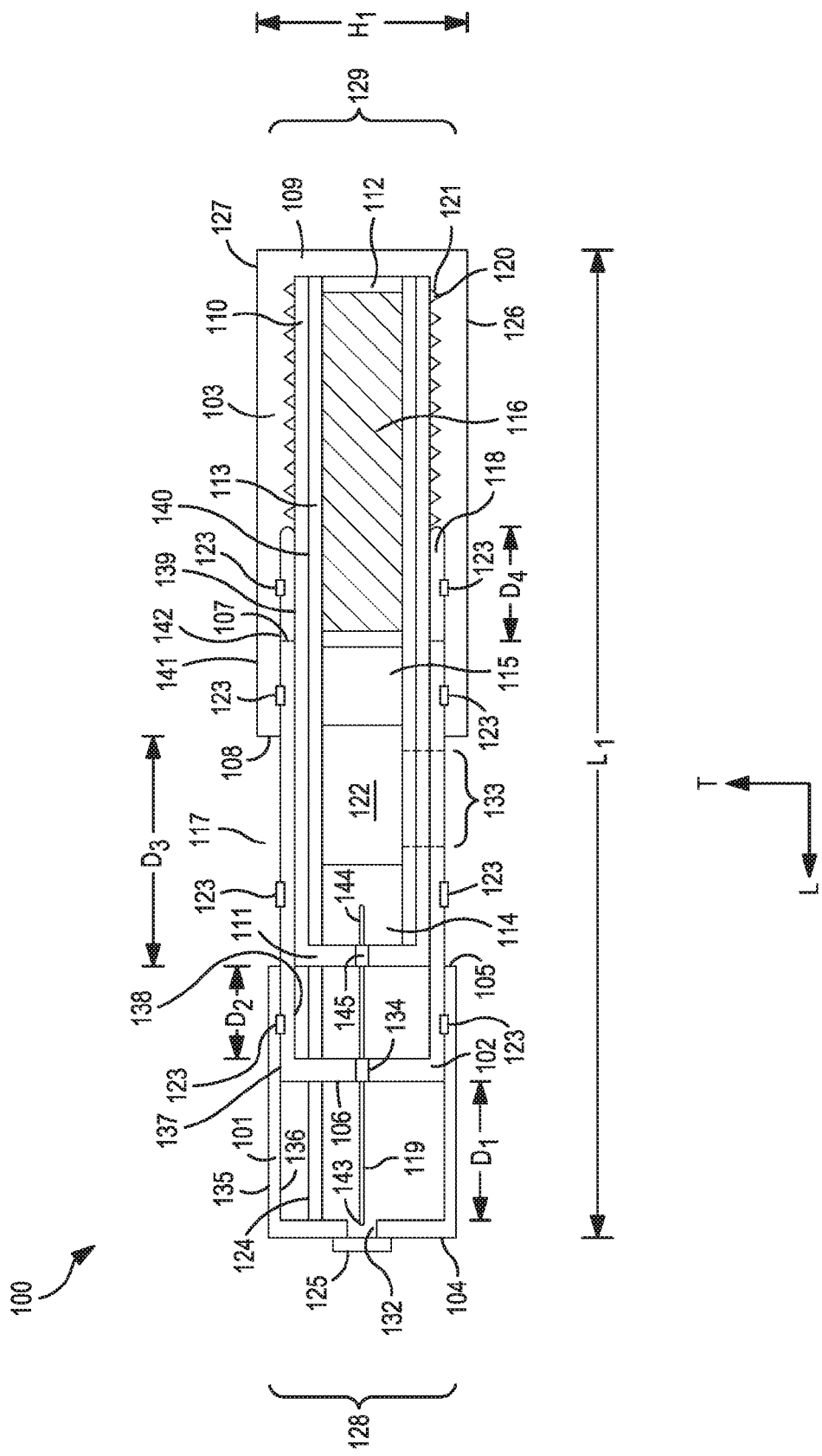
FIG. 1 depicts a longitudinal cross-sectional view of an exemplary auto-injection device having a first sleeve, a second sleeve, an ampoule containing a fluid medicament contained between a first stopper and a second stopper, and a needle according to an exemplary embodiment of the present disclosure before use.

Repeat use of reference characters in the present specification and drawings is intended to represent the same or analogous features or elements of the present invention.

DETAILED DESCRIPTION OF REPRESENTATIVE EMBODIMENTS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present disclosure is directed to an auto-injection device for the intramuscular delivery of a fluid medicament and a method for delivering fluid medicament using an auto-injection device. The auto-injection device can deliver the fluid medicament in two steps, where a surface of skin is pierced in a first step, while the fluid medicament is delivered to the intramuscularly in a separate and subsequent second step. Such a configuration, where the fluid medicament is delivered after the needle pierces the skin and has been inserted into the muscle, ensures that the fluid medicament is properly delivered to the musculature, rather than to an area just below the skin's surface (e.g., intradermal or subcutaneously), which can occur with the simultaneous needle injection and delivery of the fluid medicament. In other words, by inserting the needle into the muscle in a first step and delivering the fluid medicament in a second step, the auto-injection device of the present disclosure enables delivery of the fluid medicament in an accurate and effective manner.

The fluid medicament contained within the auto-injection device can be any fluid medicament that can be delivered intramuscularly. In one particular embodiment, such as when the auto-injection device is used to treat anaphylaxis, the fluid medicament can be epinephrine. Epinephrine, also known as 4-[(1R)-1-Hydroxy-2-(methylamino)ethyl]-1,2-benzenediol, is the active principle of the adrenal medulla and an endogenous catecholamine which acts directly on both alpha and beta adrenergic receptors. When used in pharmaceutical compositions, epinephrine can act as a nonselective alpha and beta adrenergic agonist and can work rapidly to improve breathing, stimulate the heart, raise dropping blood pressure, reverse hives, and reduce swelling of the face, lips, and throat. Uses for epinephrine include emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. Epinephrine can also be used to increase blood flow in ACLS during CPR, as an adjunct to local anesthesia, and for radiographic uses. Although the use of the auto-injection device of the present disclosure to deliver epinephrine is described herein, it is to be understood that the auto-injection device and its method of use can be utilized in conjunction with any fluid medicament that can be delivered intramuscularly.

Referring to FIGS. 1-4, an auto-injection device according to embodiments of the present disclosure is shown prior to use and during use. Generally, FIG. 1 depicts a cross-sectional view of an exemplary auto-injection device 100 prior to use, where the auto-injection device 100 includes a first sleeve 101 in a first position, a second sleeve 102 in a first position, an ampoule 113 containing a fluid medicament 122 contained between a first stopper 114 and a second stopper 115, and a needle 119 according to an exemplary embodiment of the present disclosure before use. The auto-injection device 100 defines a longitudinal direction L in which the first sleeve 101, second sleeve 102, ampoule 113, and needle 119 extend, as well as a transverse direction T. The auto-injection device can include a viewing window 133 through which the ampoule 113 can be observed, where the fluid medicament 122 is visible through the viewing window 133 prior to use and the second stopper 115 is visible through the viewing window 133 after use and delivery of the fluid medicament 122.

As shown in FIG. 1, the first sleeve 101 and second sleeve 102 are located towards a proximal end 128 of the auto-injection device 100. The first sleeve 101 includes a proximal end 104, a distal end 105, an outer surface 135, and an inner surface 136. The second sleeve 102 includes a proximal end 106, a distal end 107, an outer surface 137, and an inner surface 138. The proximal end 104 of the first sleeve 101 includes an opening 132 over which a needle cover 125 (plastic film or foil) can be applied to ensure sterility of the needle 119 prior to use, where the needle 119 is contained within an interior space formed between the proximal end of 104 of the first sleeve and a proximal end 106 of the second sleeve 102 and is thus unexposed along the longitudinal direction L. As discussed in more detail below, the needle 119 is movable with respect to the first sleeve 101 such that its proximal end 143 can pass through the opening 132, but is fixed to the proximal end 106 of the second sleeve 102 between its proximal end 143 and its distal end 144, such as with an epoxy or other suitable sealant material 134. Meanwhile, the distal end 144 of the needle 119 is disposed within the first stopper 114 but does not extend past the first stopper (i.e., the needle 119 is fluidly isolated from the fluid medicament 122 when the first sleeve 101 and the second sleeve 102 are both in a first position). In addition, the auto-injection device 100 can include a removable safety 124 that, when installed, can lock the first sleeve 101 such that it is not movable with respect to the second sleeve 102 and can lock the second sleeve 102 such that it is not movable with respect to ampoule 113, the housing 110 (discussed in more detail below) and/or the third sleeve 103 to ensure that the needle 119 does not unintentionally pass through the opening 132. The auto-injection device 100 can also include locks 123 located along its longitudinal direction L on the first side 126 and second side 127 of the auto-injection device 100, where the locks 123 face internally and prevent reuse of the auto-injection device 100 by preventing the return of the first sleeve 101 and the second sleeve 102 to their respective first positions after the first sleeve 101 and second sleeve 102 have been moved to their second positions. As such, the locks 123 provide a safety measure to prevent the unintentional reuse of the auto-injection device 100.

Further, the auto-injection device 100 can also include a housing 110 that surrounds the ampoule 113, as well as a third sleeve 103 that is positioned at a distal end 129 of the auto-injection device 100. The housing 110 includes a proximal end 111, a distal end 112, an outer surface 139, and an inner surface 140. A portion of the needle 119 passes through an opening 145 in the housing 110 so that the distal end 144 of the needle 119 can be disposed within the first stopper 114. The third sleeve includes a proximal end 108, a distal end 109, an outer surface 141, and an inner surface 142. Female threads 121 can be disposed on the third sleeve 103 that can interface with male threads 120 disposed on the housing 110 to secure the third sleeve 103 in place. An adhesive or glue (not shown) can be used to ensure that the female threads 121 and male threads 120 are sufficiently engaged and to ensure that the auto-injection device 100 cannot be unintentionally disassembled. Further, a biasing element 116 (e.g., compression spring, a compressed gas, etc.) can be included within the ampoule 113 and positioned between the second stopper 115 and a distal end 112 of the housing 110, where the biasing element 116 can be in a compressed state when the first sleeve 101 and the second sleeve 102 are in their respective first positions.

In its unused state, the auto-injection device is assembled such that a distance D1 exists between the proximal end 104 of the first sleeve 101 and the proximal end 106 of the second sleeve 102, a distance D2 exists between the proximal end 106 of the second sleeve 102 and the proximal end 111 of the housing 110, a first gap 117 extending a distance D3 exists between a distal end 105 of the first sleeve 101 and a proximal end 108 of the third sleeve 103, and a second gap 118 extending a distance D4 exists between a distal end 107 of the second sleeve 102 and the beginning of the female threaded portion 121 of the third sleeve 103. Regardless of the particular dimensions of the auto-injection device 100, distance D3 is greater than distance D1 and distance D4 is greater than distance D2.

Moreover, in its assembled, unused state, the auto-injection device 100 can have a maximum length L1 in the longitudinal direction L of less than 150 millimeters, such as less than 100 millimeters. For instance, the auto-injection device 100 can have a maximum length ranging from about 60 millimeters to about 100 millimeters, such as from about 70 millimeters to about 95 millimeters, such as from about 80 millimeters to about 90 millimeters. Further, the auto-injection device can have a maximum height H1 in the transverse direction T ranging from about 10 millimeters to about 30 millimeters, such as from about 12 millimeters to about 25 millimeters, such as from about 15 millimeters to about 20 millimeters. Additionally, the first sleeve 101, second sleeve 102, third sleeve 103, and housing 110 can be formed from any suitable plastic (e.g., polycarbonate, a polyolefin such as polyethylene or polypropylene, polystyrene, etc.), while the ampoule 113 can be formed from glass.

Figure 2:
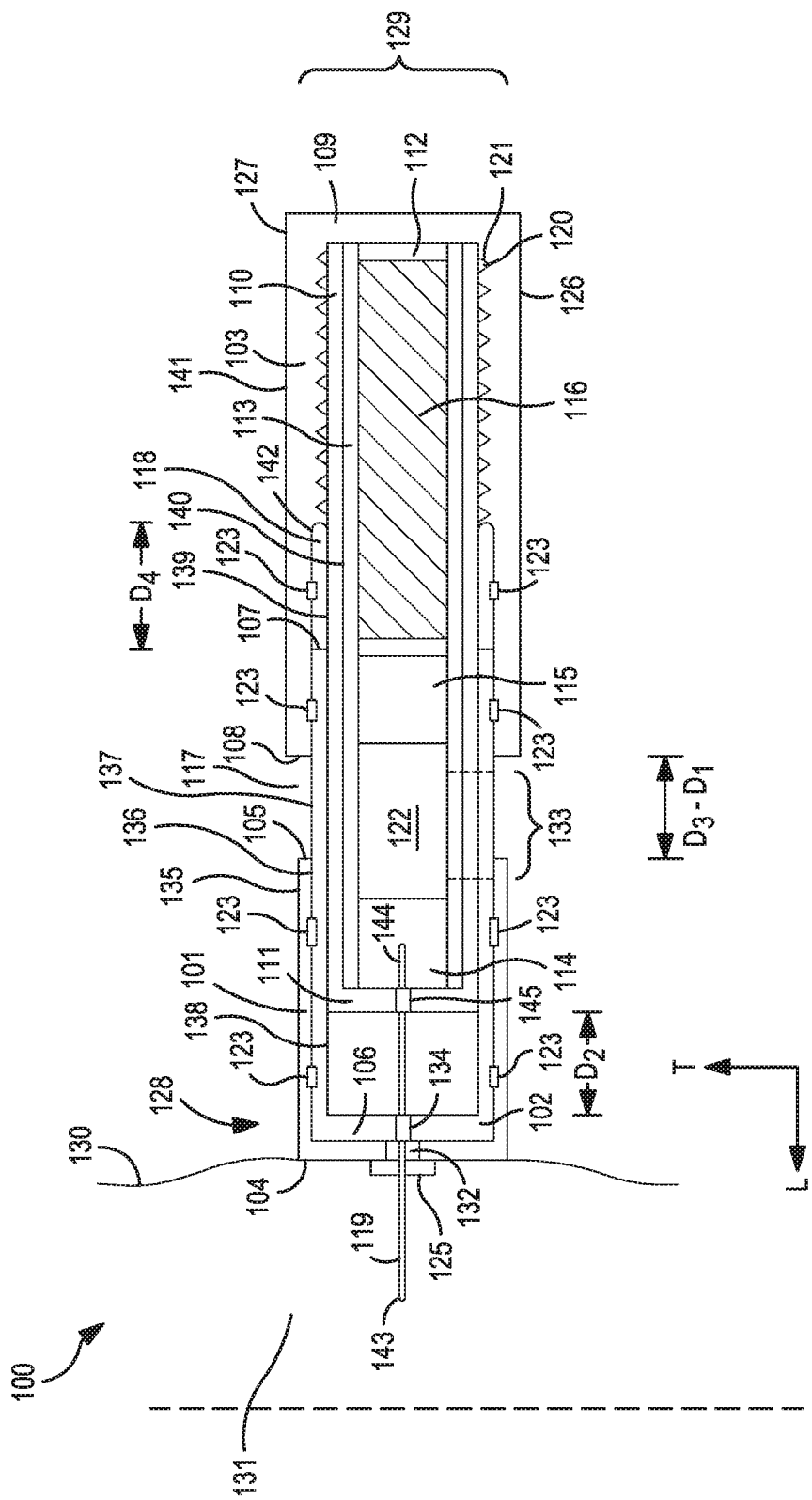
FIG. 2 depicts the auto-injection device of FIG. 1 when its first sleeve has moved from a first position to a second position.

Next, FIG. 2 depicts the auto-injection device of FIG. 1 after the safety 124 has been removed, the needle cover 125 has been pierced, and the first sleeve 101 has moved from its first position to a second position so that a proximal end 143 of the needle 119 is exposed along the longitudinal direction L and has pierced the needle cover 125 and a surface of skin 130 and contacted muscle 131. Although the needle cover 125 is shown as being pierced, it is also to be understood that, in the alternative, the needle cover 125 can be removed. To arrive at its second position, the proximal end 104 of the first sleeve 101 is pressed against the surface of skin 130 while holding the third sleeve 103 at the distal end 129 of the auto-injection device so that the longitudinal direction L of the auto-injection device 100 is generally perpendicular to the surface of skin 130. An inner surface 136 of the first sleeve 101 is slidably engaged with an outer surface 137 of the second sleeve 102 so that the first sleeve 101 is movable along the longitudinal direction L relative to the ampoule 113 until the proximal end 104 of the first sleeve 101 contacts the proximal end 106 of the second sleeve 102 and whereby the proximal end 143 of the needle 132 has passed through the opening 132 in the proximal end 104 of the first sleeve 101 and has pierced through the needle cover 125 and the surface of skin 130 and has entered the muscle 131. In this regard, the distance D1 is now essentially zero since the proximal end 104 of the first sleeve 101 and the proximal end 106 of the second sleeve 102 are now in contact.

Additionally, as shown in FIG. 2, the first gap 117 having an original distance D3 now spans a distance that has been reduced by the distance D1, such that the first gap 117 now has a distance that is equal to D3 minus D1. As shown in FIG. 2, the needle 119 remains fixed to the proximal end 106 of the second sleeve 102 between its proximal end 143 and its distal end 144, such as with an epoxy or other suitable sealant material 134. Meanwhile, the distal end 144 of the needle 119 remains disposed within the first stopper 114 but does not extend past the first stopper (i.e., the needle 119 is fluidly isolated from the fluid medicament 122 when the first sleeve 101 is in a second position and the second sleeve 102 is in a first position).

Figure 3:
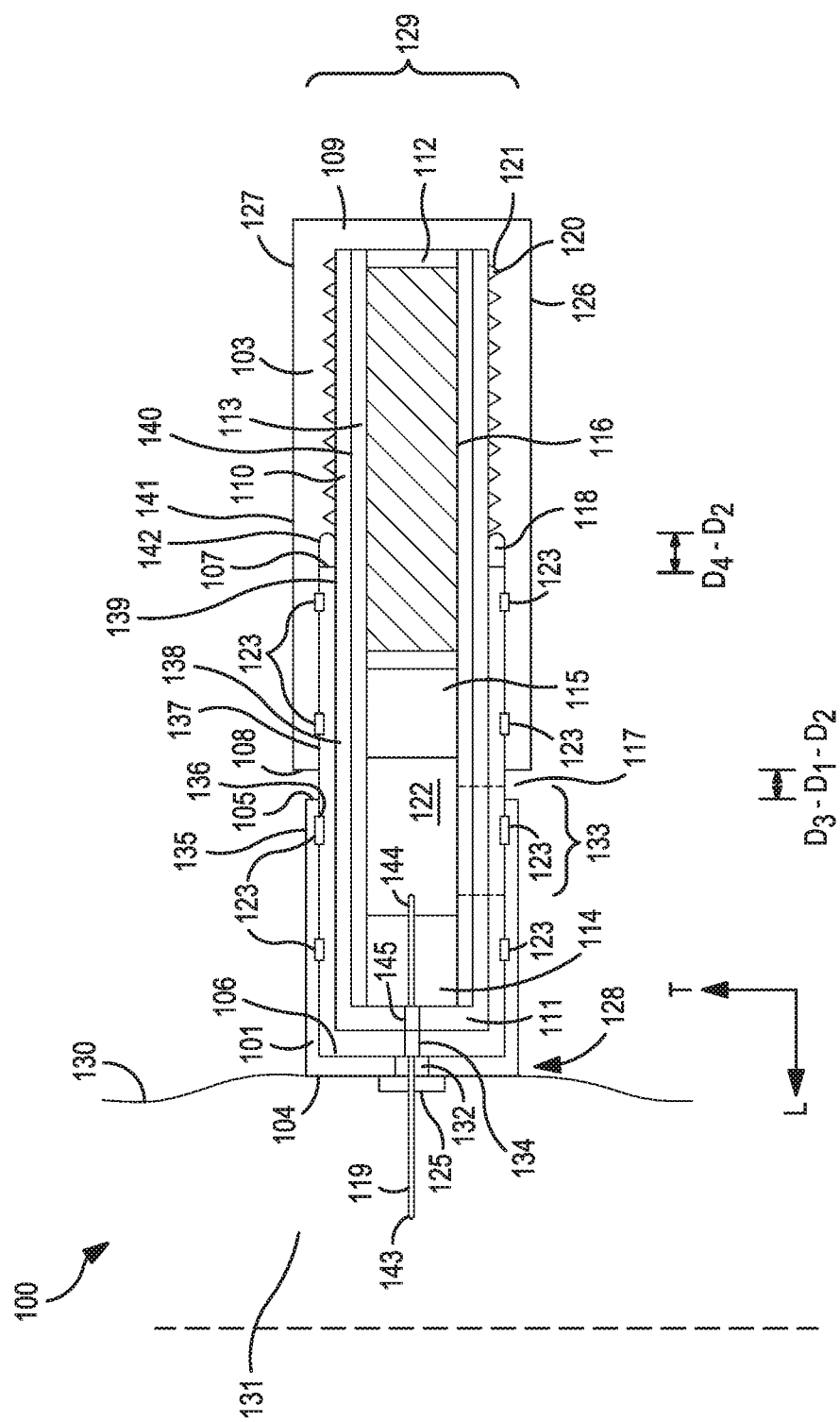
FIG. 3 depicts the auto-injection device of FIG. 1 when its second sleeve has moved from a first position to a second position.

FIG. 3 depicts the auto-injection device of FIG. 1 after its second sleeve 102 has moved from its first position to a second position so that a distal end 144 of the needle 119 has pierced through the first stopper 114 so that the distal end 144 of the needle 119 is in fluid contact with the fluid medicament 122 contained within the ampoule 113 and the needle 119 is thus in fluid communication with the fluid medicament 122. So that the second sleeve 102 can arrive at its second position, the proximal end 104 of the first sleeve 101 is again pressed against the surface of skin 130 while holding the third sleeve 103 at the distal end 129 of the auto-injection device so that the longitudinal direction L of the auto-injection device 100 is generally perpendicular to the surface of skin 130. Now that the proximal end 104 of the first sleeve 101 and the proximal end 106 of the second sleeve 102 are in contact as described above in FIG. 2, an inner surface 138 of the second sleeve 102 is slidably engaged with an outer surface 139 of the housing 110 toward the proximal end 111 of the housing 110 and an outer surface 137 of the second sleeve 102 is slidably engaged with inner surface 142 of the third sleeve 103 towards the distal end 109 of the third sleeve 103 so that the second sleeve 102 is movable along the longitudinal direction L relative to the ampoule until the proximal end 106 of the second sleeve 102 contacts the proximal end 111 of the housing 110. In addition, as the proximal end 106 of the second sleeve 102 contacts the proximal end 111 of the housing 110, the distal end 144 of the needle 132 passes through the first stopper 114 so that the distal end 144 of the needle is now in fluid communication with the fluid medicament 122. In this regard, the distance D2 is now zero since the proximal end 106 of the second sleeve 102 and the proximal end 111 of the housing 110 are now in contact.

Referring still to FIG. 3, the second gap 118 having an original distance D4 now spans a distance that has been reduced by the distance D2, such that the second gap 118 now has a distance that is equal to D4 minus D2. Meanwhile, the first gap 117 having an original distance D3 now spans a distance that has been further reduced by the distance D2, such that the first gap 117 now has a distance that is equal to D3 minus D1 minus D2. As shown in FIG. 3, the needle 119 still remains fixed to the proximal end 106 of the second sleeve 102 between its proximal end 143 and its distal end 144, such as with an epoxy or other suitable sealant material 134. Meanwhile, the distal end 144 of the needle 119 passes through the first stopper 114 and extends past the first stopper (i.e., the needle 119 is in fluid contact with the fluid medicament 122 when the first sleeve 101 is in its second position and the second sleeve 102 is also in a second position), whereby the fluid medicament 122 can now pass from the ampoule 113, through the distal end 144 of the needle 119, and out of the proximal end 143 of the needle 119 into the muscle 131.

Figure 4:
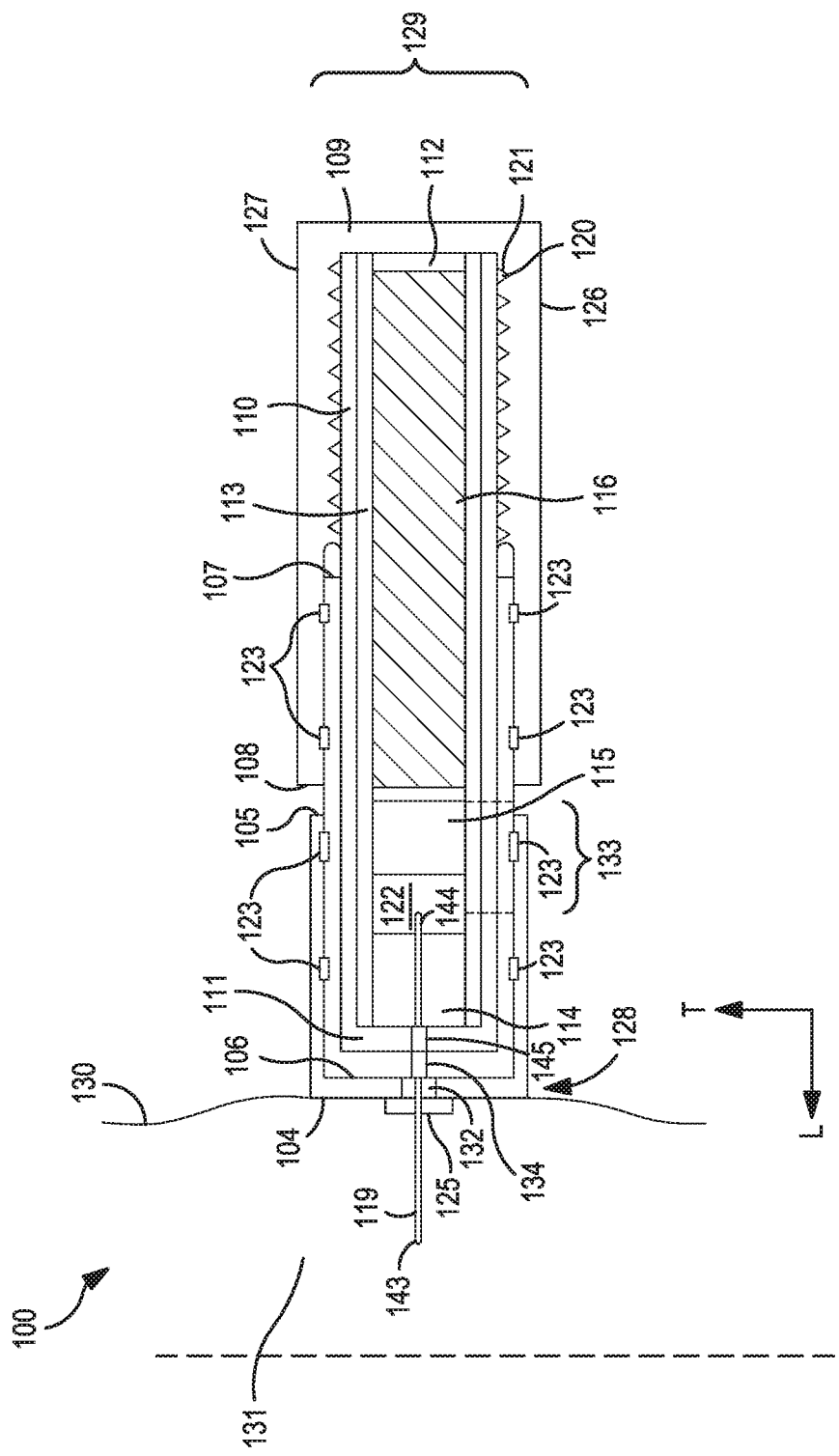
FIG. 4 depicts the auto-injection device of FIG. 1 after a biasing element has caused movement of the second stopper towards the first stopper to deliver the fluid medicament.

In addition, FIG. 4 depicts the auto-injection device of FIG. 1 after the biasing force of the biasing element 116 has caused movement of the second stopper 115 towards the first stopper 114 to facilitate delivery of the fluid medicament 122 into the muscle 130. Referring to FIGS. 1-3, the biasing element 116 (e.g., a spring, compressed gas, etc.) is initially in a compressed state. However, as shown in FIG. 4, as the distal end 144 of the needle 119 contacts the fluid medicament 122 contained within the ampoule 113, the biasing element 116 expands in the longitudinal direction L to facilitate the delivery of the fluid medicament 122 to the muscle 131, whereby the second stopper 115 moves towards the first stopper 114 and the proximal end 128 of the auto-injection device 100. As the fluid medicament 122 is delivered, the second stopper 115 becomes visible in the viewing window 133, which indicates to the user that the fluid medicament 122 has been properly delivered. Although not shown, the second stopper 115 is moveable towards the first stopper 114 until it reaches the distal end 144 of the needle 119 to ensure delivery of a full dose of the fluid medicament 122.

As described above, the present disclosure contemplates an auto-injection device having a needle that pierces a surface of skin and is inserted into the muscle in a first step and that delivers fluid medicament intramuscularly in a second step. Such a two-step auto-injection device, where the fluid medicament is delivered after the needle pierces the skin and has been inserted into the muscle, ensures that the fluid medicament is properly delivered to the musculature, rather than to an area just below the skin's surface (e.g., intradermal or subcutaneously), which can occur with the simultaneous needle injection and delivery of the fluid medicament. In other words, by inserting the needle into the muscle in a first step and delivering the fluid medicament in a second step, the auto-injection device of the present disclosure enables delivery of the fluid medicament in an accurate and effective manner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An auto-injection device defining a longitudinal direction, the auto-injection device comprising:
   an ampoule, the ampoule comprising a fluid medicament contained between a first stopper located towards a proximal end of the ampoule and a second stopper located towards a distal end of the ampoule, wherein the ampoule is completely contained within a housing during use of the auto-injection device;
   a first sleeve movable along the longitudinal direction relative to the ampoule;
   a second sleeve at least partially surrounding the ampoule and movable along the longitudinal direction relative to the ampoule, wherein the second sleeve is movable from a proximal end of the auto-injection device towards a distal end of the auto-injection device; and
   a needle located at the proximal end of the auto-injection device, wherein the needle is fixed to the second sleeve;
   wherein the first sleeve is movable along the longitudinal direction relative to the second sleeve and the ampoule between a first position and a second position, wherein in the first position the needle is unexposed along the longitudinal direction and in the second position the needle is exposed along the longitudinal direction, and
   wherein the second sleeve is movable along the longitudinal direction relative to the ampoule between a first position and a second position, wherein in the first position the needle is fluidly isolated from the fluid medicament and in the second position the needle is in fluid communication with the fluid medicament.

2. The auto-injection device of claim 1, wherein the auto-injection device is a two-step fluid medicament delivery device, wherein the needle pierces a surface of skin in a first step and the fluid medicament is delivered in a subsequent second step.

3. The auto-injection device of claim 2, wherein, in the first step, the needle pierces the surface of skin when the first sleeve is in the second position.

4. The auto-injection device of claim 3, wherein an opening is located along a proximal end of the first sleeve, wherein the proximal end of the needle is movable through the opening when the first sleeve is moved to the second position.

5. The auto-injection device of claim 2, wherein, in the second step, fluid medicament is delivered intramuscularly when the second sleeve is in the second position.

6. The auto-injection device of claim 1, wherein a biasing element is contained within the ampoule towards the distal end of the ampoule, wherein the biasing element exerts a biasing force on the second stopper towards the first stopper.

7. The auto-injection device of claim 1, further comprising a removable safety, wherein the removable safety prevents movement of the first sleeve from the first position to the second position, prevents movement of the second sleeve from the first position to the second position, or both when not removed.

8. The auto-injection device of claim 1, wherein the ampoule comprises glass.

9. The auto-injection device of claim 1, wherein the housing comprises a plastic.

10. The auto-injection device of claim 1, wherein the first sleeve and the second sleeve each comprise a plastic.

11. The auto-injection device of claim 1, wherein the fluid medicament contains epinephrine.

12. The auto-injection device of claim 1, wherein the auto-injection device has a length in the longitudinal direction of less than 150 millimeters.

13. A two-step method for delivering a dose of fluid medicament via an auto-injection device, wherein the auto-injection device defines a longitudinal direction and comprises an ampoule containing a fluid medicament contained between a first stopper located towards a proximal end of the ampoule and a second stopper located towards a distal end of the ampoule, wherein the ampoule is always completely contained within a housing during use of the auto-injection device; a first sleeve movable in the longitudinal direction relative to the ampoule; a second sleeve at least partially surrounding the ampoule and movable along the longitudinal direction relative to the ampoule, wherein the second sleeve is movable from a proximal end of the auto-injection device towards a distal end of the auto-injection device; and a needle located at the proximal end of the auto-injection device, wherein the needle is fixed to the second sleeve; the method comprising:
   positioning the proximal end of the auto-injection device against a surface of skin, wherein the longitudinal direction of the auto-injection device is generally perpendicular to the surface of skin;
   piercing the surface of skin and underlying tissue with the needle by pressing the proximal end of the auto-injection device against the surface of skin until the first sleeve moves from a first position to a second position in a first step; and
   delivering the fluid medicament intramuscularly by pressing the proximal end of the auto-injection device against the surface of skin until the second sleeve moves from a first position to a second position in a second step.

14. The method of claim 13, wherein the proximal end of the first sleeve contacts a proximal end of the second sleeve when the first sleeve is in the second position.

15. The method of claim 13, wherein the proximal end of the second sleeve contacts the proximal end of a housing surrounding the ampoule when the second sleeve is in the second position.

16. The method of claim 13, wherein a proximal end of the first sleeve includes an opening covered with a material to maintain sterility of the auto-injection device prior to use, wherein the material is removed prior to positioning the proximal end of the auto-injection device against the surface of skin, or wherein the material is pierced by the needle by pressing the proximal end of the auto-injection device against the surface of skin until the first sleeve moves from the first position to the second position in the first step.

17. The method of claim 13, wherein a removable safety prevents the first sleeve from sliding against the second sleeve, prevents the second sleeve from sliding against the ampoule, or both, wherein the removable safety is removed prior to positioning the proximal end of the auto-injection device against the surface of skin.

18. The method of claim 13, wherein a biasing element is contained within the ampoule towards the distal end of the ampoule, wherein the biasing element exerts a biasing force on the second stopper towards the first stopper to facilitate delivery of the fluid medicament when the second sleeve is in the second position.

19. The method of claim 13, wherein the fluid medicament contains epinephrine.

* * * * *